United States Patent [19]

Oka et al.

[11] Patent Number: 5,836,887
[45] Date of Patent: Nov. 17, 1998

[54] PHYSICAL INFORMATION MONITOR SYSTEM HAVING MEANS FOR DETERMINING REFERENCE RANGE FOR ABNORMALITY DETERMINATION, BASED ON MOVING AVERAGE OF PREVIOUSLY OBTAINED VALUES

[75] Inventors: Tohru Oka, Ichinomiya; Makoto Takakura, Sapporo, both of Japan

[73] Assignee: Colin Corporation, Komaki, Japan

[21] Appl. No.: 716,604

[22] Filed: Sep. 19, 1996

[51] Int. Cl.[6] ......................................................... A61B 5/00
[52] U.S. Cl. .......................... 600/494; 600/495; 600/493
[58] Field of Search ................................ 126/630, 633–4, 126/664–6, 661.07, 670–678, 677, 680, 687, 716, 719, 721.2, 736, 748, 903

[56] References Cited

U.S. PATENT DOCUMENTS

| | | | |
|---|---|---|---|
| 4,197,854 | 4/1980 | Kasa . | |
| 4,245,648 | 1/1981 | Trimmer et al. | 128/672 |
| 4,479,494 | 10/1984 | McEwen | 128/682 |
| 4,889,131 | 12/1989 | Salem et al. | 128/903 |
| 4,944,305 | 7/1990 | Takatsu et al. | 128/680 |
| 4,951,679 | 8/1990 | Harada | 128/672 |
| 5,226,416 | 7/1993 | Bethune et al. | 128/716 |
| 5,253,648 | 10/1993 | Walloch | 128/682 |
| 5,279,303 | 1/1994 | Kawamura et al. . | |
| 5,319,355 | 6/1994 | Russek | 128/903 |
| 5,343,868 | 9/1994 | Kurscheidt et al. | 128/672 |
| 5,355,893 | 10/1994 | Mick et al. | 128/719 |
| 5,464,012 | 11/1995 | Falcone | 128/672 |

FOREIGN PATENT DOCUMENTS

A-2 281 780   3/1995   United Kingdom .

*Primary Examiner*—Robert L. Nasser
*Attorney, Agent, or Firm*—Oliff & Berridge, PLC

[57] ABSTRACT

A physical information monitor system comprising: (a) physical information obtaining means for successively obtaining physical information values of a living subject; (b) moving average calculating means for continuously calculating a moving average of the physical information values successively obtained by the physical information obtaining means; (c) reference range determining means for determining a reference range on the basis of the moving average calculated by the moving average calculating means; and (d) abnormality determining means for determining whether one of the physical information values which is currently obtained by the physical information obtaining means is abnormal, the abnormality determining means generating an abnormality signal when the currently obtained physical information value is outside the reference range.

4 Claims, 5 Drawing Sheets

PHYSICAL INFORMATION MONITOR SYSTEM HAVING MEANS FOR DETERMINING REFERENCE RANGE FOR ABNORMALITY DETERMINATION, BASED ON MOVING AVERAGE OF PREVIOUSLY OBTAINED VALUES

BACKGROUND OF THE INVENTION

1. Field of the Invention

The present invention relates to a physical information monitor system for monitoring successively obtained physical information of living subjects.

2. Discussion of the Related Art

For monitoring the physical condition of a patient (living subject) in an operating room or ICU (Intensive Care Unit), there is proposed a physical information monitor system adapted to successively measure one or more physical parameters of the patient, such as blood pressure, pulse rate, blood oxygen saturation and temperature, and to generate an abnormality signal indicative of abnormality of any physical parameter when the physical parameter is outside a predetermined reference range.

In general, the conventional physical information monitor system as described above has abnormality determining means for determining whether the obtained physical information is outside a predetermined reference range. The abnormality determining means generates an abnormality signal when the obtained physical information is outside the reference range. The abnormality signal may be visually indicated by suitable characters given on a display, or by a flickering or colored display area in which the measured abnormal value is displayed, for instance. Alternatively, the abnormality may be indicated by a sound or voice.

The abnormality determining means relatively frequently generates the abnormality signal if the above-described reference range is set to be relatively narrow. The frequent generation of the abnormality signal undesirably lowers the reliability of the monitor system. In view of this drawback, the reference range is usually set to be relatively wide for the purpose of improving the reliability of the abnormality signal. However, when the reference range is set to be relatively wide, it is difficult to detect an abrupt or rapid change in the physical information values with a high response. This undesirably causes a delay in implementing a suitable medical treatment for the patient whose physical information has abruptly deteriorated. For instance, in the case where the blood pressure of the patient is abruptly lowered due to an influence of an antihypertensive agent administered to the patient during an operation, the abrupt drop of the blood pressure of the patient cannot be found in the conventional monitor system until the blood pressure value has been lowered below the lower limit of the reference range, which is set to be relatively low.

SUMMARY OF THE INVENTION

It is therefore an object of the present invention to provide a physical information monitor system which is capable of accurately monitoring the physical information of a living subject, and quickly detecting a change in the physical information.

The above object may be attained according to a principle of the present invention which provides a physical information monitor system comprising: (a) physical information obtaining means for successively obtaining physical information values of a living subject; (b) moving average calculating means for continuously calculating a moving average of the physical information values successively obtained by the physical information obtaining means; (c) reference range determining means for determining a reference range on the basis of the moving average calculated by the moving average calculating means; and (d) abnormality determining means for determining whether one of the physical information values which, is currently obtained by the physical information obtaining means is abnormal, the abnormality determining means generating an abnormality signal when the currently obtained physical information value is outside the reference range.

In the monitor system constructed according to the present invention, the moving average calculating means continuously calculates the moving average of the physical information values successively obtained by the physical information obtaining means. On the basis of the calculated moving average, the reference range is determined by the determining means. The abnormality determining means determines whether the currently obtained physical information value is outside the determined reference range, and generates the abnormality signal if the physical information value is outside the reference range.

According to the present monitor system constructed as described above, the reference range used for determining the abnormality of the physical information is determined on the basis of the moving average of the successively obtained physical information values. This arrangement is capable of quickly detecting a change in the physical information values while assuring highly reliable determination of the abnormality of the physical information, even when the amount of change in the physical information values is relatively small.

According to one preferred form of the present invention, the moving average calculating means calculates a first moving average of the physical information values successively obtained during a predetermined first time period, and a second moving average of the physical information values successively obtained during a predetermined second time period which is longer than the predetermined first time period, the reference range determining means determining a first reference range on the basis of the first moving average and a second reference range on the basis of the second moving average, the abnormality determining means generating a first abnormality signal if the current physical information value obtained by the physical information obtaining means is outside the first reference range, and a second abnormality signal different from the first abnormal signal if the current physical information value is outside the second reference range.

The monitor system constructed according to the above preferred form of the invention is capable of detecting both of such abnormality of the physical information that arises from an abrupt change of its value and such abnormality of the physical information that arises from a gradual change of its value.

BRIEF DESCRIPTION OF THE DRAWINGS

The above and optional objects, features and advantages of the present invention will be better understood by reading the following detailed description of a presently preferred embodiment of the invention when considered in connection with the accompanying drawings in which.

DETAILED DESCRIPTION OF THE PREFERRED EMBODIMENT

Figure 1:
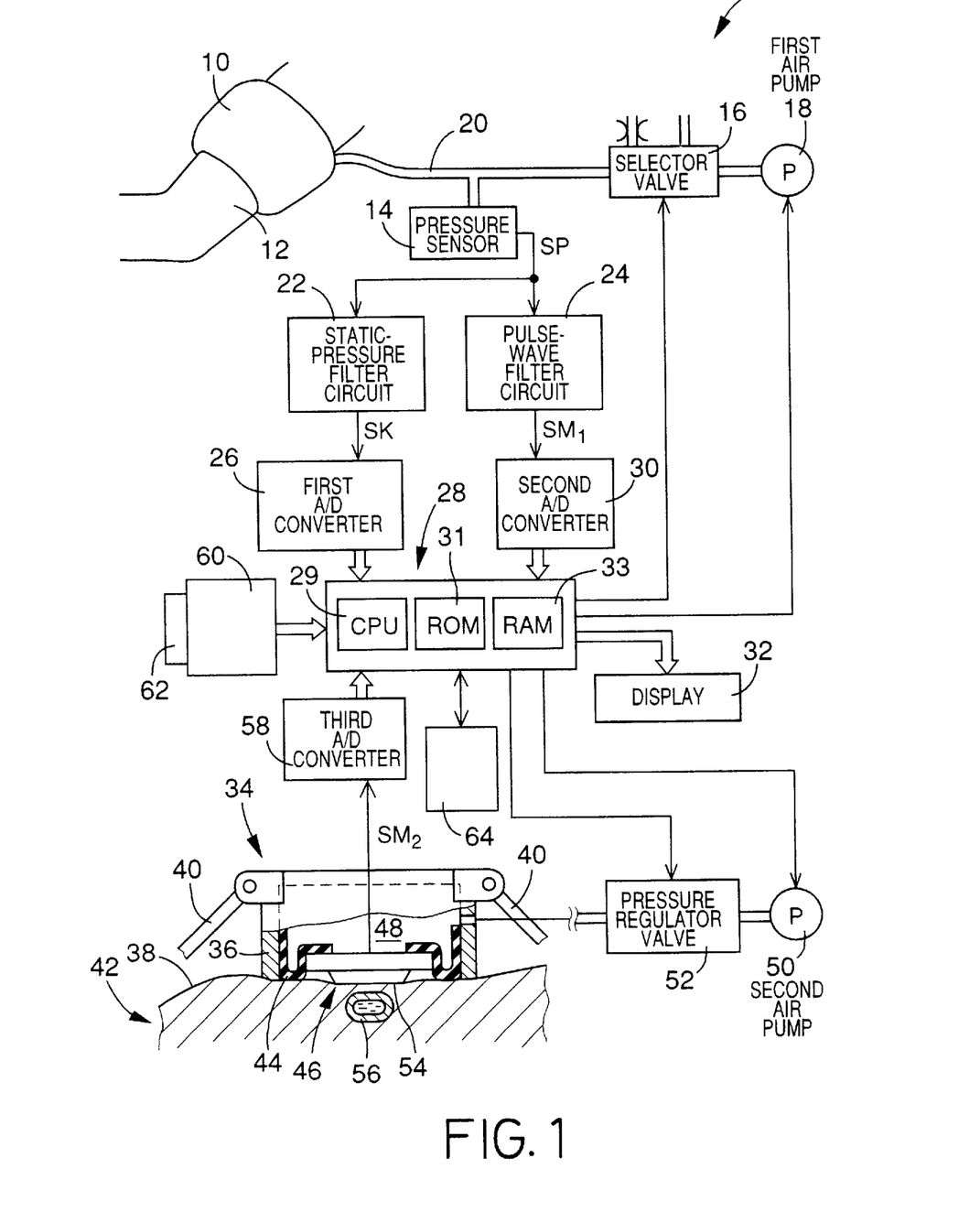
FIG. 1 is a diagrammatic block diagram of a blood pressure monitor system according to one embodiment of the present invention.

Referring first to FIG. 1, there is shown a blood pressure (BP) monitor system 8 constructed according to one embodiment of the present invention. In FIG. 1, the reference numeral 10 denotes an inflatable cuff constituted by an elongate fabric bag and a rubber bag accommodated in the elongate fabric bag. The cuff 10 is worn on a patient such that it is wound on an upper arm 12 of the patient, for example. A pressure sensor 14, a selector valve 16 and a first air pump 18 are connected to the cuff 10 via a conduit piping 20. The selector valve 16 is selectively placed in an inflation position, a slow-deflation position, and a rapid-deflation position. In the inflation position, the selector valve 16 permits pressurized air to be supplied from the first air pump 18 to the cuff 10. In the slow-deflation position, the selector valve 16 permits the pressurized air to be slowly discharged from the cuff 10. In the rapid-deflation position, the selector valve 16 permits the pressurized air to be rapidly discharged from the cuff 10.

The pressure sensor 14 detects an air pressure in the cuff 10 and supplies an electric signal SP representative of the detected pressure to a static-pressure filter circuit 22 and a pulse-wave filter circuit 24. The static-pressure filter circuit 22 has a low-pass filter and transmits a static component of the signal SP as a cuff-pressure signal SK to a control device 28 via a first analog to digital (A/D) converter 26.

The pulse-wave filter circuit 24 has a band-pass filter and transmits an oscillating component of the signal SP as a cuff pulse wave signal $SM_1$ to the control device 28 via a second analog to digital (A/D) converter 30. The cuff pulse wave signal $SM_1$ is representative of a pulse wave, i.e., an oscillatory pressure wave which is produced from a brachial artery of the patient in synchronism with the heartbeat of the patient and transmitted to the cuff 10. In the present embodiment, the cuff 10, pressure sensor 14 and pulse-wave filter circuit 24 cooperate with each other to function as a pulse wave sensor for obtaining the blood pressure of the patient.

The control device 28 is constituted by a so-called microcomputer which includes a central processing unit (CPU) 29, a read only memory (ROM) 31, a random access memory (RAM) 33 and an input and output (I/O) port not shown. The CPU 29 performs signal processing operations according to control programs stored in the ROM 31 by utilizing a temporary data storage function of the RAM 33, and generates drive signals through the I/O port so as to control the selector valve 16 and first air pump 18.

The present monitor system 8 further includes a pulse wave probe 34. The probe 34 is set on a wrist 42 located downstream of the arterial vessel of either one of the two upper arms 12, on which the cuff 10 is worn or is not worn. The probe 34 includes a container-like housing 36 which is detachably set on a body surface 38 of the wrist 42 with a pair of bands 40, 40 fastened round the wrist 42, such that the open end of the housing 36 contacts the body surface 38 of the wrist 42. A pulse wave sensor 46 is supported by the housing 36 via a flexible diaphragm 44, such that the pulse wave sensor 46 is displaceable relative to the housing 36 and is movable out of the housing 36 through its open end. The housing 36, diaphragm 44 and pulse wave sensor 46 cooperate with each other to define a pressure chamber 48, to which pressurized air is supplied from a second air pump 50 via a pressure regulator valve 52. Thus, the pulse wave sensor 46 is pressed against the body surface 38 with a pressing force $P_{HD}$ corresponding to an air pressure in the pressure chamber 48.

The pulse wave sensor 46 includes a plurality of semiconductor pressure-sensing elements (not shown) provided on one of opposite surfaces of a semiconductor substrate consisting of a single crystal of silicon, which one surface serves as a contact surface 54 of the pulse wave sensor 46. The pulse wave sensor 46 is pressed at the contact surface 54 against the body surface 38 of the wrist 42, to detect the oscillatory pressure wave, i.e., pulse wave, which is produced by a radial artery 56 and transmitted to the body surface 38 and the contact surface 54. The pulse wave sensor 46 generates a probe pulse wave signal $SM_2$ representative of the detected pulse wave. The probe pulse wave signal $SM_2$ is supplied to the control device 28 via a third analog to digital (A/D) converter 58.

The CPU 29 of the control device 28 operates according to the control programs stored in the ROM 31, for applying drive signals to the second air pump 50 and the pressure regulator valve 52 so as to adjust the air pressure in the pressure chamber 48, in other words, to adjust the pressing force $P_{HD}$ of the pulse wave sensor 46 which acts on the body surface 38. In monitoring the blood pressure of the patient, the CPU 29 determines an optimum pressing force $P_{HDP}$ of the pulse wave sensor 46, on the basis of the pulse waves obtained while the air pressure in the pressure chamber 48 is continuously changed. The pressure regulator valve 52 is controlled so as to maintain the air pressure in the pressure chamber 48 at an optimum level corresponding to the determined optimum pressing force $P_{HDP}$.

Figure 3:
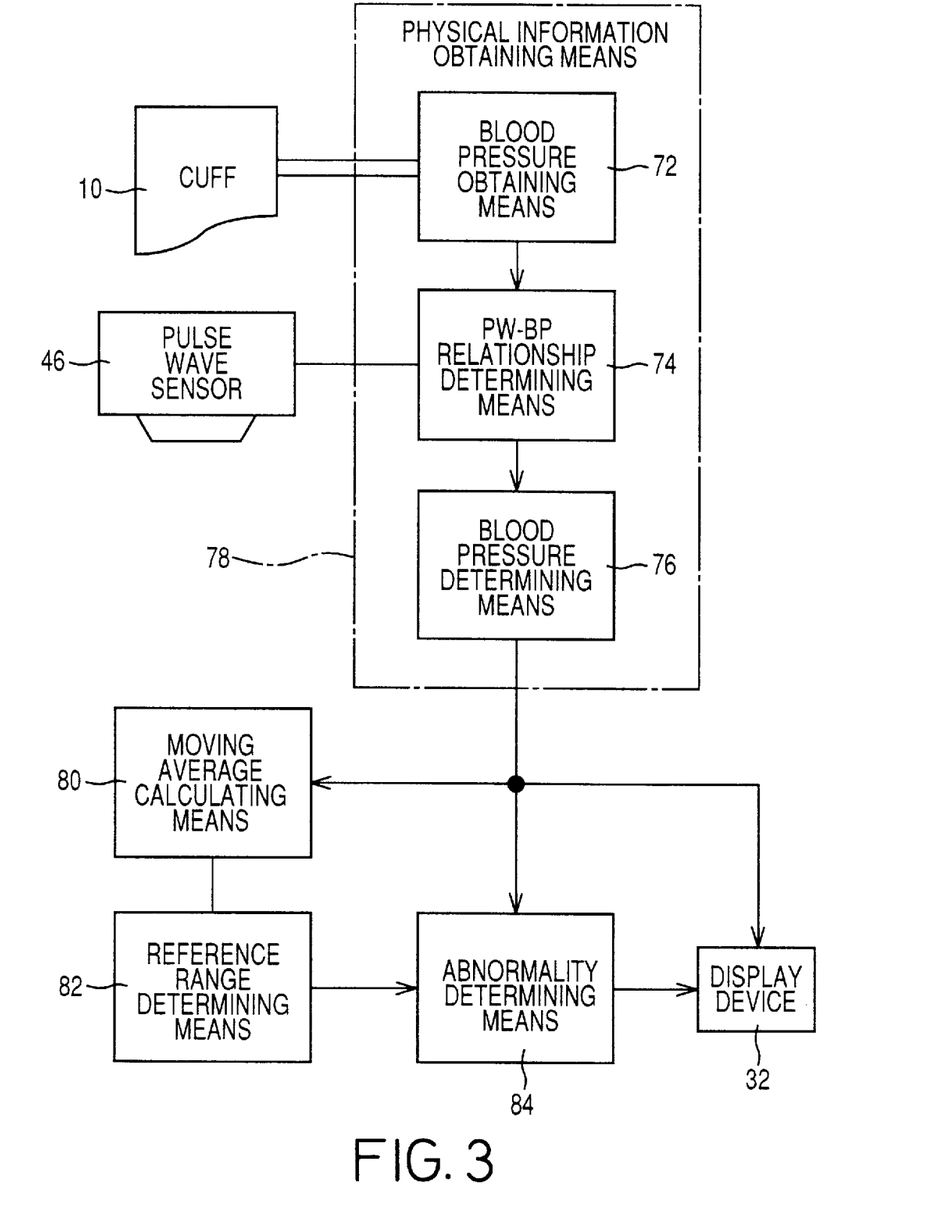
FIG. 3 is a block diagram schematically showing various functions of a control device used in the blood pressure monitor system of FIG. 1.

FIG. 3 illustrates various functions of the control device 28 of the present BP monitor system 8, which includes the above-indicated cuff 10 and pulse wave sensor 46. The BP monitor system 8 further includes physical information obtaining means 78, moving average calculating means 80, reference range determining means 82 and abnormality determining means 84. The physical information obtaining means 78 incorporates blood pressure (BP) obtaining means 72, relationship determining means 74 and blood pressure determining means 76. The blood pressure (BP) obtaining means 72 is adapted to obtain a systolic blood pressure (SAP) and a diastolic blood pressure (DAP) of the patient according to a known oscillometric method (JIS T 1115). Described in detail, after the pressure in the cuff 10 is first increased up to a predetermined target value (e.g., about 180 mmHg) higher by a suitable amount than an expected or estimated systolic blood pressure of the patient, the pressure in the cuff 10 is slowly lowered at a rate of about 3 mmHg/sec. The SAP and DAP values are determined on the basis of a change in the magnitudes of successive pulses of the pulse wave obtained by the pulse-wave filter circuit 24 while the pressure in the cuff 10 is slowly lowered. When the blood pressure measurement is completed, the pressure in the cuff 10 is released.

The pulse wave sensor 46 is preferably worn on the wrist 42 of one of the arms 12 of the patient on which the cuff 10 is not wound, so that the pulse wave sensor 46 is pressed against the body surface 38 of the wrist 42 to detect the pulse wave generated from the radial artery of the wrist.

Figure 2:
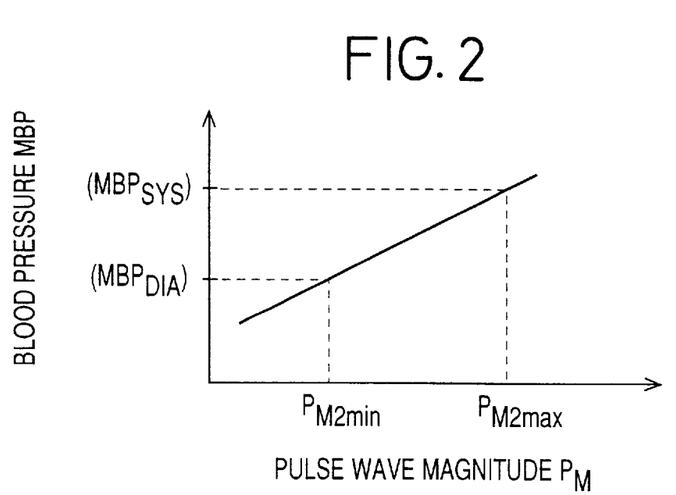
FIG. 2 is a graph representing a relationship between a pulse wave magnitude $P_M$ and a monitored blood pressure MBP.

The relationship determining means 74 of the physical information obtaining means 78 is adapted to determine a relationship between a magnitude PM of the pulse wave detected by the pulse wave sensor 46 and the blood pressure determined by the BP obtaining means 72. The relationship between the pulse wave magnitude PM and the blood pressure (hereinafter referred to as "PW-BP relationship") is indicated in a graph of FIG. 2 by way of example, and represented by the following equation:

$$MBP = A \cdot PM + B,$$

wherein

MBP: monitored blood pressure;

A: a constant which represents a gradient; and

B: a constant which represents an intercept.

The blood pressure determining means 76 of the physical information obtaining means 78 is adapted to determine a monitored systolic blood pressure $MBP_{SYS}$ and a monitored diastolic blood pressure $MBP_{DIA}$ according to the determined PW-BP relationship, based on the magnitude PM of each pulse wave detected by the pulse wave sensor 46, i.e., on the basis of a maximum pulse wave magnitude (upper peak) $P_{M2max}$ and a minimum pulse wave magnitude (lower peak) $P_{M2min}$. The determined blood pressure values MBP ($MBP_{SYS}$ and $MBP_{DIA}$) are indicated on a display device 32, together with a pressure pulse wave indicative of the blood pressure of the patient, i.e., a waveform of the blood pressure. Thus, the physical information obtaining means 78 is adapted to obtain the blood pressure (BP) waveform as an example of the physical information of the living subject.

The moving average calculating means 80 continuously calculates a moving average of a plurality of the physical information values which are successively obtained by the physical information obtaining means 78. On the basis of the calculated moving average, the reference range is determined by the determining means 82. The abnormality determining means 84 determines whether the physical information value currently obtained by the obtaining means 78 is outside the determined reference range. When the current physical information value is outside the reference range, the abnormality determining means 84 generates an abnormality signal so that the abnormality is visually indicated on a display device 32 or the like.

Preferably the moving average calculating means 80 is adapted to calculate a first moving average $P_{AV1}$ and a second moving average $P_{AV2}$. Described more specifically, the calculating means 80 calculates the first average $P_{AV1}$ of the physical information values obtained during a predetermined first time period, which is a relatively short time duration of about ten seconds to several tens of seconds. Similarly, the calculating means 80 calculates the second moving average $P_{AV2}$ of the physical information values obtained during a predetermined second time period, which is sufficiently longer than the first time period for the first moving average $P_{AV1}$. The second time period is determined to be several tens of minutes, for instance. The reference range determining means 82 determines, on the basis of the calculated first moving average $P_{AV1}$, a first reference range whose lower limit and upper limits are equal to $(P_{AV1}-\alpha)$ and $(P_{AV2}+\alpha)$, respectively. Similarly, the determining means 82 determines, on the basis of the calculated second moving average $P_{AV2}$, a second reference range whose lower and upper limits are equal to $(P_{AV2}-\beta)$ and $(P_{AV2}+\beta)$, respectively. The abnormality determining means 84 generates a first abnormality signal when the physical information value currently obtained by the obtaining means 78 is outside the determined first reference range, and a second abnormality signal when the current physical information value is outside the determined second reference range. For example, the first abnormality signal is used to generate an alarm sound having a relatively low frequency while the second abnormality signal is used to generate an alarm sound having a relatively high frequency.

There will be described the operation of the control device 28 referring to the flow chart of FIG. 4.

Figure 4:
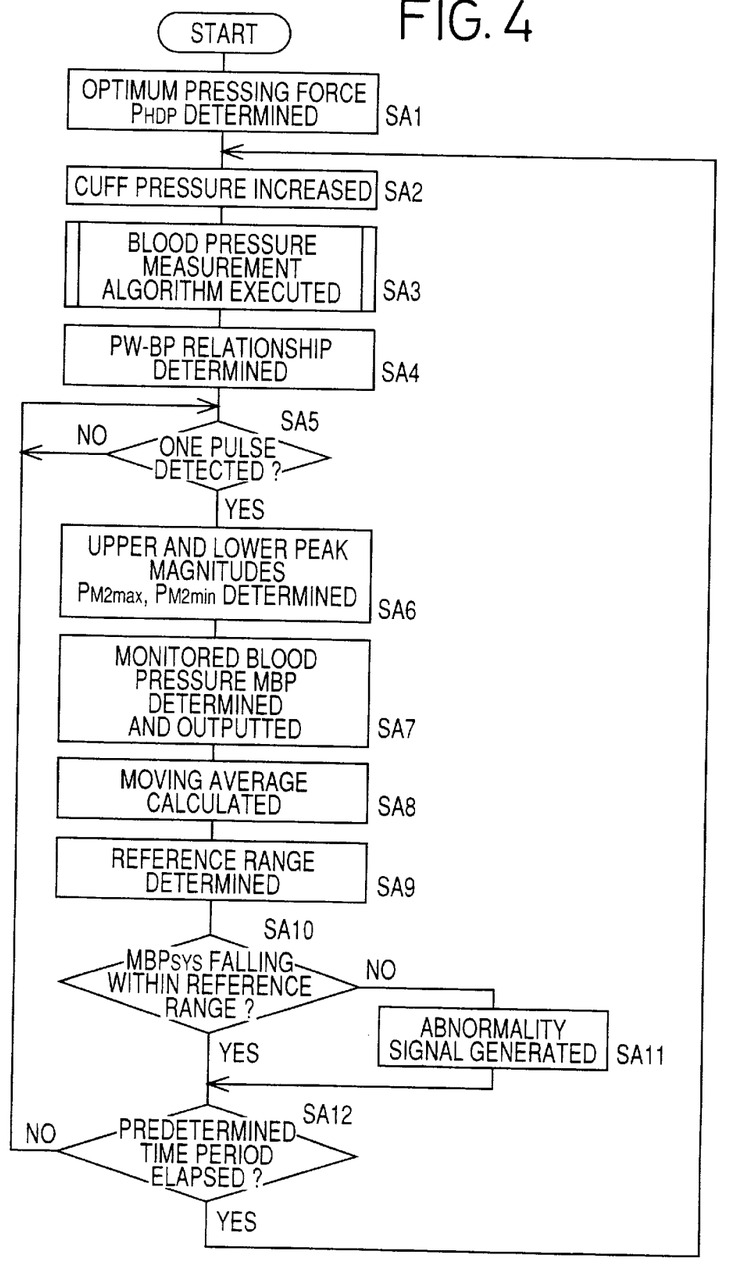
FIG. 4 is a flow chart representing a control routine executed by the control device in the blood pressure monitor system of FIG. 1.

A control routine illustrated in the flow chart of FIG. 4 is initiated with step SA1 in which the air pressure in the pressure chamber 48 is slowly raised, and the CPU 29 determines the optimum air pressure in the pressure chamber 48, at which the amplitude of a pulse detected by the pulse wave sensor 46 is maximized. The air pressure in the chamber 48 is held at the determined optimum level so that the pressing force of the pulse wave sensor 46 is maintained at the optimum value $P_{HDP}$.

Step SA1 is followed by step SA2 in which the pressure in the cuff 10 is raised for effecting the blood pressure measurement in the following step SA3 corresponding to the BP obtaining means 72. In this step SA3, the blood pressure of the patient is measured according to a predetermined blood pressure measuring algorithm. Described in detail, following the increase of the cuff pressure in step SA2, the selector valve 16 is placed in the inflation position and the first air pump 18 is actuated so as to increase the pressure in the cuff 10 up to a target value (e.g., 180 mmHg) higher by a suitable amount than the estimated systolic blood pressure of the patient. Subsequently, the first air pump 18 is turned off and the selector valve 16 is switched from the inflation position to the slow-deflation position so as to slowly decrease the pressure in the cuff 10 at a rate of 3 mmHg/sec. The systolic blood pressure (SAP), mean blood pressure (MAP) and diastolic blood pressure (DAP) are determined based on variation of the amplitudes of successive pulses of the cuff pulse wave signal SM1 obtained during the slow decreasing of the cuff pressure, according to a well-known oscillometric blood pressure determining algorithm, for example. Further, the pulse rate (PR) is determined based on an interval between successive adjacent pulses of the cuff pulse wave signal SM1. The determined SAP, MAP, DAP and PR values are indicated on the display 32, and the selector valve 16 is switched from the slow-deflation position to the rapid-deflation position, whereby the pressure in the cuff 10 is rapidly lowered.

The control flow then goes to step SA4 corresponding to the PW-BP relationship determining means 74 so as to obtain a relationship between the magnitude (absolute value) of each pulse of the pulse wave detected by the pulse wave sensor 46 (i.e., magnitude of the probe pulse wave signal SM2) and the blood pressure values SAP, DAP measured by using the cuff 10 in step SA3. In other words;, one pulse of the probe pulse wave signal SM2 from the pulse wave sensor 46 is read to determine a maximum and a minimum magnitude $P_{M2max}$, $P_{M2min}$ of that pulse. Subsequently, the PW-BP relationship determining means 74 determines the relationship between the pulse wave magnitude PM and the monitored blood pressure MBP as indicated in the graph of FIG. 2, on the basis of the determined maximum and minimum pulse wave magnitudes $P_{M2max}$, $P_{M2min}$, and the systolic and diastolic blood pressure values SAP, DAP obtained by using the cuff 10 in step SA3.

Figure 5:
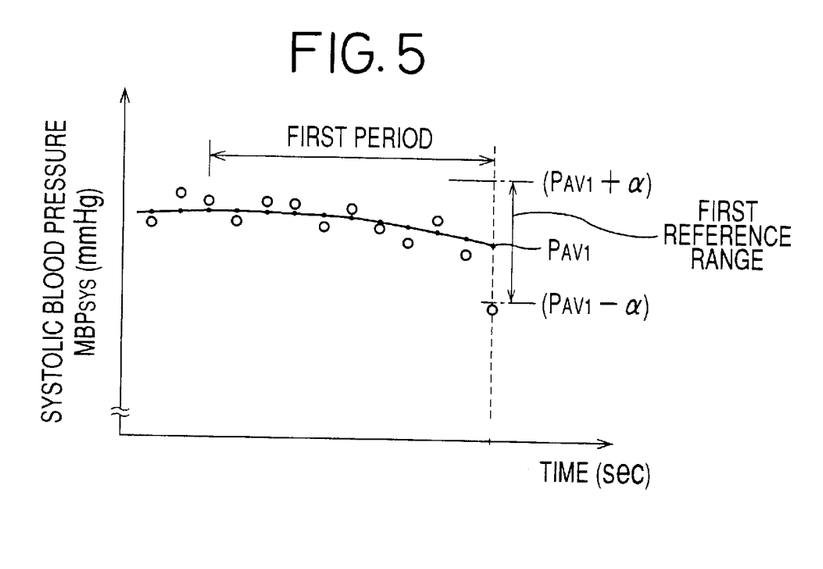
FIG. 5 is a graph indicating an example of a first reference range which is obtained as a result of an operation of the monitor system according to the control routine of FIG. 4.
Figure 6:
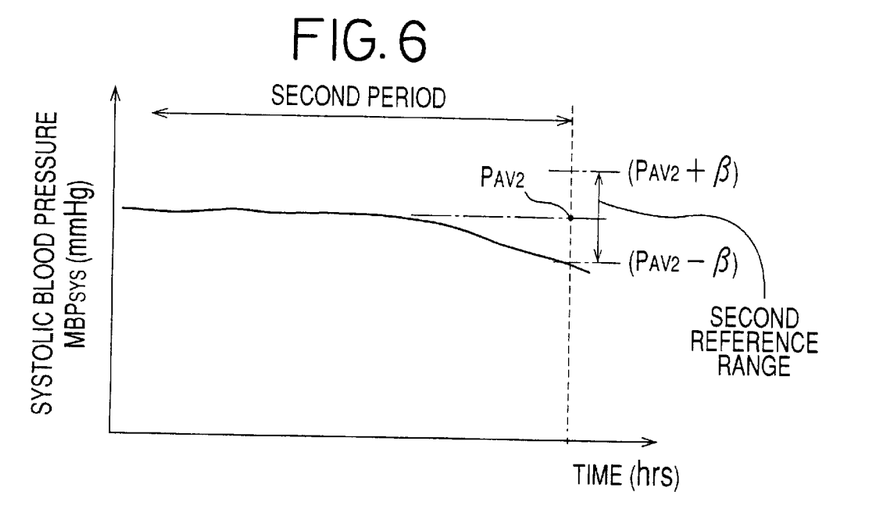
FIG. 6 is a graph indicating an example of a second reference range which is obtained as a result of an operation of the monitor system according to the control routine of FIG. 4.

Step SA4 is followed by step SA5 to determine whether one pulse of the probe pulse wave signal SM2 has been supplied from the pulse wave sensor 46. As long as a negative decision is obtained in step SAS, this step is repeatedly implemented. If an affirmative decision is obtained in step SA5, the control flow goes to steps SA6 and SA7 corresponding to the blood pressure determining means 76, so as to determine the maximum and minimum magnitudes (upper and lower peaks) of the pulse of the probe pulse wave signal SM2 received from the pulse wave sensor 46 which is pressed against the body surface 38 with the above-described optimum pressing force $P_{HDP}$. Further, a monitored systolic blood pressure $MBP_{SYS}$ and a monitored diastolic blood pressure $MBP_{DIA}$ are determined based on the maximum and minimum magnitudes $P_{M2max}$ and $P_{M2min}$ of the pulse of the probe pulse wave signal SM2, according to the PW-BP relationship (as shown in the graph of FIG. 2) which has been obtained in step SA4 as described above. The determined monitored systolic and diastolic blood pressure values $MBP_{SYS}$ and $MBP_{DIA}$ are indicated on the display device 32. In the present embodiment, the successively determined systolic blood pressure values $MBP_{SYS}$ are graphically represented as shown in FIGS. 5 and 6, so as to show a change of the $MBP_{SYS}$ values.

The control flow then goes to step SA8 corresponding to the moving average calculating means 80 to calculate the first moving average $P_{AV1}$ and the second moving average $P_{AV2}$ as described below. That is, the calculating means 80 calculates the first moving average $P_{AV1}$ of the physical information values which are obtained during the first period of a few seconds to several tens of seconds and which include the latest BP value, e.g., the $MBP_{SYS}$ value, obtained in step SA7. Similarly, the calculating means 80 calculates the second moving average $P_{AV2}$ of the physical information values obtained during the second period of several tens of minutes, which is sufficiently longer than the first period wherein the first moving average $P_{AV1}$ is obtained.

Step SA8 is followed by step SA9 corresponding to the reference range determining means 82, wherein the first and second reference ranges are respectively determined based on the first and second moving averages $P_{AV1}$, $P_{AV2}$ determined in step SA8. The first reference range is determined for the purpose of quickly detecting the abnormality of the blood pressure due to a relatively abrupt change thereof. For instance, the first reference range is determined such that the range has a lower limit defined as $(P_{AV1}-\alpha)$ and an upper limit defined as $(P_{AV1}+\alpha)$, as shown in the graph of FIG. 5. The value a is equal to a few percent to about twenty percent of the first moving average $P_{AV1}$. The second reference range is determined for the purpose of detecting the abnormality of the blood pressure which arises from a relatively gradual change thereof. For instance, the second reference range is determined such that the lower limit is equal to $(P_{AV2}-\beta)$ and the upper limit is equal to $(P_{AV2}+\beta)$, as shown in the graph of FIG. 6. The value $\beta$ is equal to a few percent to about twenty percent of the second moving average $P_{AV2}$.

The control flow then goes to step SA10 corresponding to the abnormality determining means 84 to determine whether the currently obtained systolic blood pressure $MBP_{SYS}$ falls within the first reference range and whether the systolic blood pressure MBPSYS falls within the second reference range. If a negative decision is obtained in step SA10, SA11 is implemented to generate an abnormality signal depending upon the determination in step SA10. Described more specifically, when the current $MBP_{SYS}$ deviates from the first reference range, the abnormality determining means 84 generates a first abnormality signal used to provide a visible or audible indication of a relatively rapid change in the blood pressure. On the other hand, when the $MBP_{SYS}$ deviates from the second reference range, the abnormality determining means 84 generates a second abnormality signal used to provide a visible or audible indication of a relatively gradual change in the blood pressure. The visible or audible indication according to the second abnormality signal is made different from that according to the first abnormality signal, so that the second abnormality can be easily distinguished from the first abnormality.

Step SA11 is followed by step SA12. This step SA 12 is effected immediately following step SA10 if an affirmative decision is obtained in step SA10. Step SA12 is provided to determine whether a predetermined time period has elapsed after the commencement of the blood pressure measurement by using the cuff 10 in step SA3. For example, the predetermined time period is several tens of minutes. If a negative decision is obtained in step SA12, the control flow goes back to step SA5 and the following steps for determining the monitored systolic and diastolic blood pressure $MBP_{SYS}$ and $MBP_{DIA}$ of the pulse wave signal SM2 and indicating the determined blood pressures $MBP_{SYS}$ and $MBP_{DIA}$ on the display device 32. On the other hand, if an affirmative decision is obtained in step SA12, the control flow goes back to step SA2 and the following steps so as to update the PW-BP relationship.

According to the present embodiment described above, the moving average calculating means 80 corresponding to step SA8 continuously calculates the first moving average $P_{AV1}$ of the systolic blood pressure values $MBP_{SYS}$ successively obtained by the physical information obtaining means 78 corresponding to steps SA2 through SA7. On the basis of the calculated first moving average $P_{AV1}$, the reference range determining means 82 corresponding to step SA9 determines the first reference range. The abnormality determining means 84 corresponding to step SA10 determines whether the currently obtained value $MBP_{SYS}$ is outside the determined first reference range, and generates the first abnormality signal when the value $MBP_{SYS}$ is outside the first reference range. Thus, the first reference range used for determining the abnormality of the current value $MBP_{SYS}$ is determined based on the first moving average $P_{AV1}$ of the successively obtained values $MBP_{SYS}$. Accordingly, the present monitor system is capable of quickly detecting the change in the systolic blood pressure MBPSYS and accurately monitoring the blood pressure when the value $MBP_{SYS}$ abruptly changes even if the amount of change is relatively small.

In the illustrated embodiment, the calculating means 80 corresponding to step SA8 calculates the first moving average $P_{AV1}$ of the values $MBP_{SYS}$ obtained during the relatively short first time period, and the second moving average $P_{AV2}$ of the values $MBP_{SYS}$ obtained during the second time period which is sufficiently longer than the first time period. The reference range determining means 82 corresponding to step SA9 determines, on the basis of the calculated first moving average $P_{AV1}$, the first reference range defined by the upper limit of $(P_{AV1}+\alpha)$ and the lower limit of $(P_{AV2}-\alpha)$. Similarly, the determining means 82 determines, on the basis of the calculated second moving average $P_{AV2}$, the second reference range defined by the upper limit of $(P_{AV2}+\beta)$ and the lower limit of $(P_{AV2}-\beta)$. The abnormality determining means 84 corresponding to step SA10 generates the first abnormality signal when the current value $MBP_{SYS}$ is outside the first reference range between $(P_{AV1}-\alpha)$ and $(P_{AV1}+\alpha)$, while the determining means 84 generates the second abnormality signal when the current value $MBP_{SYS}$ is outside the second reference range between $(P_{AV2}-\beta)$ and $(P_{AV2}+\beta)$. Thus, the present monitor system is capable of detecting both of an abrupt and a gradual change in the systolic blood pressure $MBP_{SYS}$.

While the present invention has been described in its presently proffered embodiment, it is to be understood that the invention may be otherwise modified.

In the illustrated embodiment, the systolic blood pressure $MBP_{SYS}$ is monitored as the physical information of the patient. However, the systolic blood pressure $MBP_{SYS}$ may be replaced with the diastolic blood pressure $MBP_{DIA}$ or the mean blood pressure. Alternatively, the pulse rate, temperature, oxygen saturation, or fluctuation of these parameters (within a given time period) may be monitored by the present monitor system.

The monitor system of the illustrated embodiment is arranged to determine whether the systolic blood pressure $MBP_{SYS}$ falls within the first reference range between $(P_{AV1}-\alpha)$ and $(P_{AV1}+\alpha)$ which is determined based on the first moving average $P_{AV1}$ and whether the systolic blood pressure $MBP_{SYS}$ falls within the second reference range between $(P_{AV2}-\beta)$ and $(P_{AV2}+\beta)$ which is determined based on the second moving average $P_{AV2}$. However, the present monitor system may be modified to determine whether the systolic blood pressure $MBP_{SYS}$ is outside either one of the first and second reference ranges.

The blood pressure obtaining means 72 is adapted to determine the blood pressure according to the known oscillometric method, based on a change in the magnitude of the pulses of the pulse wave, which change is detected as the pressure in the cuff 10 is varied. However, the blood pressure obtaining means 72 may be adapted to determine the blood pressure according to the known Korotkoff-sound method in which a microphone is used to detect presence and absence of Korotkoff sounds of an artery as the pressure in the cuff 10 is changed.

It is to be understood that the present invention may be embodied with other changes, improvements and modifications which will occur to those skilled in the art without departing from the scope and spirit of the invention defined in the appended claims.

What is claimed is:

1. A physical information monitor system, comprising:

physical information obtaining means for successively obtaining physical information values of a living subject;

moving average calculating means for continuously calculating a moving average of said physical information values successively obtained by said physical information obtaining means;

reference range determining means for determining a reference range on the basis of said moving average calculated by said moving average calculating means; and abnormality determining means for determining whether one of said physical information values which is currently obtained by said physical information obtaining means is abnormal, said abnormality determining means generating an abnormality signal when the currently obtained physical information value is outside said reference range, wherein said moving average calculating means calculates a first moving average of said physical information values successively obtained during a predetermined first time period, and a second moving average of said physical information values successively obtained during a predetermined second time period which is longer than said predetermined first time period, said reference range determining means determining a first reference range on the basis of said first moving average and a second reference range on the basis of said second moving average, said abnormality determining means generating a first abnormality signal if said current physical information value obtained by said obtaining means is outside said first reference range, and a second abnormality signal different from said first abnormal signal if said current physical information value is outside said second reference range.

2. A physical information monitor system according to claim 1, wherein said predetermined first time period is on the order of tens of seconds while said predetermined second time period is on the order of tens of minutes.

3. A physical information monitor system according to claim 1, wherein said physical information obtaining means comprises:

pulse wave detecting means for detecting a pulse wave produced from an artery vessel of said living subject in synchronism with heartbeat of said subject;

blood pressure obtaining means including an inflatable cuff, for obtaining a blood pressure of said living subject;

relationship determining means for determining a relationship between a magnitude of said pulse wave detected by said pulse wave detecting means and said blood pressure obtained by said blood pressure obtaining means; and blood pressure determining means for determining a monitored systolic blood pressure ($MBP_{SYS}$) and a monitored diastolic blood pressure ($MBP_{DIA}$) based on said magnitude of said pulse wave and said relationship determined by said determining means.

4. A physical information monitor system according to claim 1, wherein said physical information comprises blood pressure of said living subject.

* * * * *